US008048882B2

(12) United States Patent
Kocsis et al.

(10) Patent No.: US 8,048,882 B2
(45) Date of Patent: Nov. 1, 2011

(54) PHARMACEUTICAL COMPOSITIONS WITH INCREASED ACTIVITY

(76) Inventors: Pal Kocsis, Budapest (HU); Istvan Tarnawa, Budapest (HU); Marta Than, Budapest (HU); Karoly Tihanyi, Budapest (HU); Gyorgy Nemeth, Debrecen (HU)

(*) Notice: Subject to any disclaimer, the term of this patent is extended or adjusted under 35 U.S.C. 154(b) by 1003 days.

(21) Appl. No.: 10/584,661

(22) PCT Filed: Dec. 18, 2004

(86) PCT No.: PCT/HU2004/000123
§ 371 (c)(1),
(2), (4) Date: Sep. 19, 2006

(87) PCT Pub. No.: WO2005/058363
PCT Pub. Date: Jun. 30, 2005

(65) Prior Publication Data
US 2007/0129370 A1    Jun. 7, 2007

(30) Foreign Application Priority Data

Dec. 19, 2003   (HU) .................................... 0304095

(51) Int. Cl.
*A61K 31/137* (2006.01)
*A61K 31/445* (2006.01)
*A61K 31/53* (2006.01)

(52) U.S. Cl. ........ 514/242; 514/243; 514/317; 514/447; 514/649

(58) Field of Classification Search .................. 514/242, 514/317, 447, 649
See application file for complete search history.

(56) References Cited

U.S. PATENT DOCUMENTS 4,614,499 A * 9/1986 Arseneault et al. ........... 434/262
5,735,817 A * 4/1998 Shantha .................. 604/100.02
6,191,142 B1 * 2/2001 Carson et al. ................. 514/307
6,673,832 B1 * 1/2004 Davar ........................... 514/466
2001/0036943 A1 * 11/2001 Coe et al. ...................... 514/220
2002/0151543 A1 * 10/2002 Barberich et al. ............ 514/221

OTHER PUBLICATIONS

Fitzgerald et al. Complications of antidepressants, anticonvulsants, and antiarrhythmics for chronic pain management. Techniques in Regional Anesthesia and Pain management, 1998. vol. 2, No. 3, pp. 119-129. ISSN:1084-208X.*
Waldman et al. The pharmacologic management of neuropathic pain. Progress in Anesthesiology, 1998 vol. 12, No. 4, pp. 55-64. ISSN: 0891-5784.*
Kaminska. New antiepileptic drugs in childhood epilepsies: Indcations and Limits. Epileptic Disorders, 2001 vol. 3, No. Spec. Issu. 2, pp. 37-46. ISSN: 1294-9361 (abstract).*
Leander, Fluoxetine, a Selective Serotonin-Uptake Inhibitor, Enhances the Anticonvulsant Effects of Phenytoin, Carbamazepine . . . (LY201116), Epilepsia 33(3): 573-576 (1992).
Raju et al., Effect of Fluoxetine on Maximal Electroshock Seizures in Mice: Acute VS Chronic Administration, Pharm. Res. 39(6): 451-454 (1999).
Rapeport et al., Absence of a Sertraline-Mediated Effect on the Pharmacodynamics of Carbamazepine, J. Clin. Psych. 57: 20-23 (1996).
PCT International Search Report for PCT/HU2004/000123, (2004).
PCT Written Opinion for PCT/HU2004/000123, (2004).
PCT International Preliminary Report on Patentability (IPER) for PCT/HU2004/000123, (2004).

* cited by examiner

*Primary Examiner* — Jennifer M Kim
(74) *Attorney, Agent, or Firm* — Rakoczy Molino Mazzochi Siwik

(57) ABSTRACT

The invention relates to novel pharmaceutical combinations with improved sodium channel blocking effect. Further, the invention relates to the use of said pharmaceutical combinations in chronic pain, in disturbances of the motor system, in epilepsy, as well as in other therapeutic fields where the use of sodium channel blockers is acceptable.

10 Claims, 3 Drawing Sheets

PHARMACEUTICAL COMPOSITIONS WITH INCREASED ACTIVITY

Figure 1:
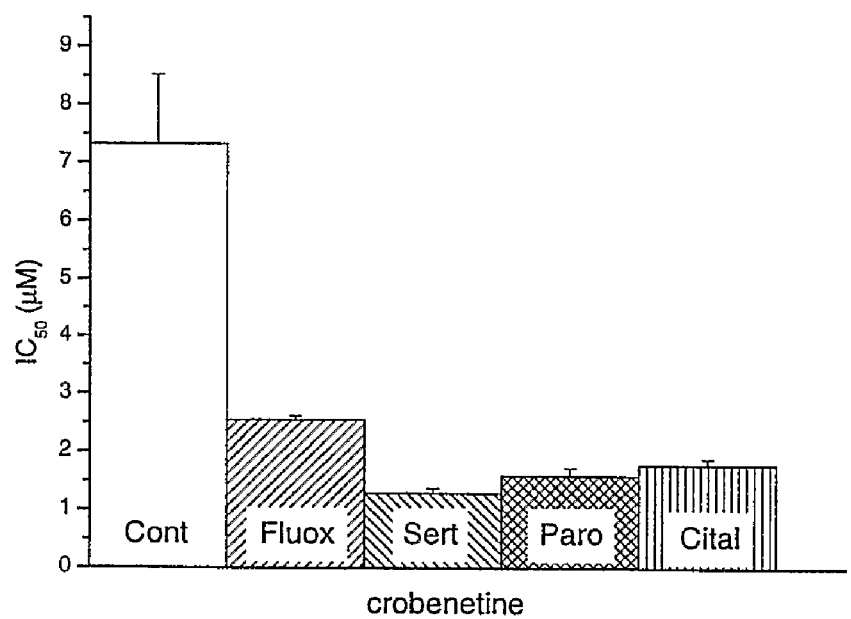

The invention relates to novel pharmaceutical combinations with increased sodium channel blocking effect. Further, the invention relates to the use of pharmaceutical combinations in chronic pain, in disturbances of the motor system, in epilepsy, as well as in other therapeutic fields where the use of sodium channel blockers is acceptable.

It is known that voltage-sensitive sodium channels play a crucial role in the generation and conduction of action potentials, thus in the regulation of excitability of the nerve cells. Sodium channels form pores in the nerve cell membrane and in response to membrane depolarization channels open for a short time and let sodium ions flow into the cell causing electric alterations. In certain diseases of the nervous system a change in the channel function can be observed resulting generally in abnormal increase of excitability of the nerve cells. Several pharmaceuticals are on the market or under development that have a beneficial effect on such diseases by blocking the voltage-dependent sodium channels.

Sodium channel blockers, such as lidocaine, are traditionally used as local anaesthetics. Some structurally similar substances (e.g. mexiletine) are used as antiarrhythmic agents. Currently some more new molecules are under development among which crobenetine proved to be effective even at very low doses (Carter, A. J. et al. Potent blockade of sodium channels and protection of brain tissue from ischemia by BIII 890 CL. Proc. Natl. Acad. Sci. USA 97: 4944-4949; 2000). The latter compound seems to be useful against neuropathic pain, too. (Laird, J. M. A. et al. Analgesic activity of a novel use-dependent sodium channel blocker, crobenetine, in mono-arthritic rats. Br. J. Pharmacol. 134: 1742-1748; 2001). Several other sodium channel blockers are effective against chronic pain (Hunter, J. C., Loughhead, D. Voltage-gated sodium channel blockers for the treatment of chronic pain. Curr. Opin. CPNS Invest. Drugs 1: 72-81; 1999). Riluzol, used for the treatment of neurodegenerative diseases has the same mechanism of action (Hurko, O., Walsh, F. S. Novel drug development for amyotrophic lateral sclerosis. J. Neurol. Sci. 180: 21-28; 2000). Recently it has been found that sodium channel blockers can be useful in the treatment of diseases accompanied by painful muscle spasms hindering patients in normal motion (Kocsis, P. et al. Mydeton: a centrally acting muscle relaxant drug of Gedeon Richter Ltd. Acta Pharm Hung 72: 49-61; 2002). Further possible fields of application are cerebral ischemia, hereditary channel diseases, tinnitus, migraine and drug abuse (Clare, J. J., et al. Voltage-gated sodium channels as therapeutic targets. Drug Discov. Today 5: 506-520; 2000). Several antiepileptics (phenyloin, carbamazepine) have been used for a long time. Sodium channel inhibitory activity was recognized as the major component of their mechanism of action. (Willow, M. et al. Voltage clamp analysis of the inhibitory actions of diphenylhydantoin and carbamazepine on voltage-sensitive sodium channels in neuroblastoma cells. Molecular Pharmacology 27: 549-558, 1985). Lamotrigine was developed with the knowledge of this mechanism of action (Leach, M. J., et al. Pharmacological studies on lamotrigine, a novel potential antiepileptic drug: II Neurochemical studies on the mechanism of action. Epilepsia 27: 490-497, 1986; Clare, J. J. et al. Voltage-gated sodium channels as therapeutic targets. Drug Discov. Today 5: 506-520; 2000).

Leander's studies showed that fluoxetine increased the anticonvulsant effect of carbamazepine, phenyloin and ameltolide in maximal electroshock seizure (MES) test in mice (Leander, J. D. Fluoxetine, a selective serotonin-uptake inhibitor enhances the anticonvulsant effects of phenyloin, carbamazepine, and ameltolide (LY201116). Epilepsia 33: 573-576, 1992.). The author concludes that fluoxetine can be useful in the treatment of those patients with depression who have epileptic problems as well since fluoxetine may enhance the effect of antiepileptic agents taken simultaneously. He makes, however, no mention of the possible mechanism of action. Similarly, Raju et al. (Raju, S. S. et al. Effect of fluoxetine on maximal electroshock seizures in mice: acute vs. chronic administration. Pharmacological Research 39: 451-454, 1999.) found that acutely applied fluoxetine caused a decrease in the anticonvulsant $ED_{50}$ value of phenyloin. On the other hand, Dailey and co-workers in their experiments found that fluoxetine given alone showed anticonvulsant activity (Dailey, J. W. et al. Neurochemical correlates of antiepileptic drugs in the genetically epilepsy-prone rat (GEPR). Life Sciences 58: 259-266, 1996.). Their further data showed that depletion of serotonin decreased the efficacy of certain antiepileptic agents (carbamazepine, antiepilepsirine), however, had no influence on the potency of phenyloin. On the other hand, other investigators emphasized that in view of the anticonvulsant effect the noradrenergic system is the most important part of the monoaminergic system (Fisher, W., Müller, M. Pharmacological modulation of central monoaminergic systems and influence on the anticonvulsant effectiveness of standard antiepileptics in maximal electroshock seizure. Biomedica Biochimica Acta 47: 631-645, 1988.). While sympatomimetics caused a marked increase in the efficiency of certain antiepileptics (phenyloin, carbamazepine), weakening of the function of the noradrenergic system caused a decrease in the potency of the studied antiepileptics. According to their results modulation of the serotonergic system has no major influence on the potency of the antiepileptics.

The opening time of the sodium channels is extremely short (1-2 ms) since after opening they will be quickly inactivated. By modification of the inactivation process excitability of the nerve cells can be influenced effectively. Recent results show that certain neurotransmitters (such as acetylcholine, serotonin, noradrenaline) may modulate channel function via G-protein coupled receptors (Carr, D. B. et al. Transmitter modulation of slow, activity-dependent alterations in sodium channel availability endows neurons with a novel form of cellular plasticity. Neuron 39: 793-806; 2003, and Li, P., Zhuo, M. Cholinergic, noradrenergic, and serotonergic inhibition of fast synaptic transmission in spinal lumbar dorsal horn of rat. Brain Res. Bull. 54: 639-647; 2001). While certain authors reported that serotonin receptor agonists may inhibit the function of sodium channels indirectly by activation of the serotonin receptors (Carr, D. B. et al. Serotonin receptor activation inhibits sodium current and dendritic excitability in prefrontal cortex via a protein kinase C-dependent mechanism. J. Neurosci. 22: 6846-6855; 2002) they didn't investigate possible synergism between sodium channel blockers and serotonergic agents. On the other hand, Rapeport reported that no synergism was found between serotonin-uptake inhibitors and sodium channel blockers (Rapeport, W. G. et al. Absence of a sertraline-mediated effect on the pharmacokinetics and pharmacodynamics of carbamazepine. Journal of Clinical Psychiatry 57 (Suppl. 1): 20-23; 1996). Published US patent application No 2002/0147196 A1 discloses favourable effect of combinations of catecholamine-uptake inhibitors with sodium channel blockers in the treatment of neuropathic pain.

In summary, experimental data published concerning a possible potentiating effect of serotonin uptake inhibitors on sodium channel blockers are controversial. While in the case of some occasional combinations potentiating effect was detected, other results suggested an opposite tendency.

Sodium channel blockers, however, possess several side effects a part of which is a consequence of the sodium channel blocking effect itself; e.g. cardiovascular (e.g. bradycardia, hypotonia) or CNS (e.g. ataxia, sedation) side effects.

Other side effects are unrelated to sodium channels and are associated with their chemical structure, e.g. higher doses of lamotrigine may induce gastrointestinal disorders, damage of the liver or skin complaints, etc. The risk of such side effects can be decreased if the effective dose of the drug is somehow lowered. Obviously, combination with an agent that potentiates the sodium blocking action is a suitable way to reach this goal.

In our experiments we have surprisingly found a marked increase in the sodium channel blocking activity when a serotonin uptake inhibitor compound is administered simultaneously; with respect to the side effects, however, this serotonergic potentiating activity appears to be less significant. Consequently, the pharmaceutical compositions according to the invention possess much more advantageous therapeutical indices than the sodium channel blockers alone. As it is shown in the rotarod test the potentiating effect of the serotonin uptake inhibitors is much less expressed or may even be absent, and thus the therapeutic indices of the combinations are considerably higher than those of the sodium channel blockers administered alone. For example the therapeutic index of lamotrigine (rotarod $ED_{50}$/MES $ID_{50}$) is 7.6, which in the presence of 10 mg/kg fluoxetine increases about threefold. The use of the combinations according to the invention may bring a progress in the therapy of epilepsy also with respect to the side effects.

Accordingly the object of the invention is a novel pharmaceutical combination showing increased activity in the therapy of diseases which are therapeutic targets for sodium channel blockers (i.e. chronic pain, certain disturbances of the motor system, epilepsy, drug or alcohol addiction, incontinence of faeces and urine, inflammation, itching, intracranial edema, ischemia and/or subsequent damage caused by reperfusion or retinopathy, as a complication glaucoma) and possessing more favourable side effect profile than the sodium channel blockers alone. In the pharmaceutical compositions according to the invention the effective therapeutic doses of the sodium channel blockers can be lowered and the clinical effectiveness thereof can be increased, respectively.

Said pharmaceutical compositions comprise as active ingredient a sodium channel blocker together with a serotonin uptake inhibitor.

Sodium channel blockers for use in the pharmaceutical compositions according to the invention are substances known to have such mechanism of action. Examples of such substances are lamotrigine, crobenetine, carbamazepine, phenyloin, tolperisone, eperisone, oxcarbamazepine, phosphenyloin, preferably lamotrigine, oxcarbamazepine, phosphenyloin, or crobenetine. Optionally the mixtures of such substances for use in carrying out the invention are also within the scope of the invention.

Serotonin uptake inhibitors which can be used are substances known to have such mechanism of action. Preferably selective serotonin uptake inhibitors are used, such as fluoxetine, paroxetine, duloxetine, sertraline, citalopram, escitalopram, most preferably fluoxetine, sertraline or citalopram. Optionally the mixtures of such substances for use in carrying out the invention are also within the scope of the invention.

The use of the salts, solvates, crystalline modifications or stereoisomers of said sodium channel blockers or serotonin uptake inhibitors as well as the mixtures thereof is also within the scope of the invention.

The pharmaceutical compositions according to the invention can be efficient in the treatment and/or prevention of chronic pain (e.g. neuropathic pain, inflamed or rheumatic origin, trigeminal neuralgia, headache, fibromyalgia), and irritable bowel syndrome (IBS), in the treatment and prevention of the disorders of the motor system (e.g. spastic diseases, essential tremor, dystonia, tinnitus, extrapyramidal disorders, tics) and neurodegenerative diseases (e.g. ALS, HIV-originated dementia, Parkinson's syndrome, Alzheimer's disease, Huntington's chorea, multiple sclerosis, prion diseases, stroke, cerebral and spinal cord injuries, cerebral ischemia), as well as in the treatment and prevention of drug or alcohol addiction, incontinence of faeces and urine, inflammation, itching, intracranial edema, ischemia and/or subsequent damage caused by reperfusion or retinopathy, as a complication glaucoma, further in treatment and prevention of different forms of epilepsy, such as partial attacks, e.g. simple partial attacks (motor, somatosensorial-sensorial, autonomic, psychic symptoms), complex partial attacks (partial onset and/or loss of conciousness) or partial attacks with secondary generalization (generalized tonic or clonic attacks), generalized attacks, such as absance (typical or atypical), myoclonus, clonic, tonic-clonic (grand mal) attacks, loss of tonus (astatic attack), as well as further forms of attack which cannot be classified (International classification of epileptic seizures, Epilepsia, 22, 489-501, 1981).

The aforementioned diseases can successfully be treated not only by simultaneous administration of the sodium channel blockers and the serotonin uptake inhibitors (in which case said substances are present in two separate compositions or in a single one, i.e. in a combination) but also by sequential administration thereof, when any of the active ingredients may be administered first.

The active agents or the pharmaceutically acceptable derivatives thereof can be used without formulation or preferably in a form suitable for medical use, particularly for human treatment.

In addition to the active agents brought into suitable form the compositions may contain one or more pharmaceutically acceptable auxiliary material(s).

The compositions may be used in oral form, parenteral form, including intravenous, subcutaneous, intradermal, intramuscular, rectal, topical, buccal, dermal or sublingual forms, as well as in forms suitable for inhalation.

Formulations suitable for oral administration can be in unit dose form, such as capsules, tablets (e.g. tablet for chewing for pediatric use), can be in powder or in granulated form, in the form of aqueous or non-aqueous solution or suspension and water-in-oil or oil-in-water emulsion form.

Tablets can be prepared in compressed or molded form optionally using one or more auxiliary materials. Compressed tablets are prepared in an appropriate compressing machine in which the powdered or granulated active ingredients are optionally mixed with known auxiliary materials, such as binders, fillers, lubricants, disintegrators, wetting agents and flavouring substances. Examples of binding agents are the syrup, acacia, gelatine, sorbitol and polyvinylpirrolidone. Examples of fillers are different hydroxymethylcellulose fillers, lactose, sugar, microcrystalline cellulose, corn starch, calcium phosphate or hydroxymethylcellulose. Examples of lubricants are the magnesium stearate, stearic acid, talc, polyethylene glycol or silica gel. Examples of disintegrators are the potato starch or sodium glycolate. Molded tablets can be prepared from the mixture of powdered active agents and an inert liquid solvent in an appropriate molding machine. Tablets optionally may be coated by methods known in the pharmaceutical industry. Tablets with slow or controlled release can also be prepared.

Compositions for oral administration may also be in liquid form, such as aqueous or oily suspensions, solutions, emulsions, syrups or elixir. Such compositions may be prepared also in dry form which can be brought into the liquid form by suitable means just before treatment.

Said liquid formulations may contain known additives, such as suspending agents (sorbitol, syrup, methylcellulose, glucose syrup, gelatine, hydroxyethylcellulose, carboxymethylcellulose, aluminium stearate gel or edible hydrogenated fats), emulsifying agents (lecithin, sorbitan monooleate, acacia), non-aqueous materials (oil of sweet almond, fractionated coconut oil, esters, propylene glycol, ethyl alcohol), preservatives (methyl or propyl-p-hydroxybenzoate, sorbitol) or flavouring additives.

Compositions in suppository form may contain traditional vehicles, such as cocoa butter, solid fats, polyethylene glycol or glycerol and derivatives thereof.

Compositions for parenteral use are aqueous or non-aqueous sterile solutions for injection and may contain antioxidants, buffers, bactericides and substances dissolved in isotonic solution. The composition is then filled e.g. in ampules (one or more unit dose) or can be stored in lyophilized form.

Examples of compositions suitable for topical use are in the form of cream, gel, ointment or transdermal plaster.

Examples of intranasal compositions are sprays, dusts or drops.

Composition suitable for use in the treatment may be an aerosol spray containing in addition to the active ingredient a propellant, such as carbon dioxide 1,1,1-trifluorethane, 1,1,1,2,3,3,3,-heptafluorpropane or the like.

BIOLOGICAL DATA

Inhibition of the Spinal Reflex

Our experiments were performed according to the methods described by Otsuka and Konishi (Otsuka, M., Konishi, S. Electrophysiology of mammalian spinal cord in vitro. Nature 252, 733-734; 1974), with slight modifications (Kocsis, P. et al. Participation of AMPA- and NMDA-type excitatory amino acid receptors in the spinal reflex transmission, in rat. Brain Research Bulletin 60: 81-91; 2003). The $L_5$ dorsal root of the isolated, hemisected spinal cord preparation was stimulated by supramaximal electrical impulse and the reflex potential from the $L_5$ ventral root was recorded. Different components of the reflex potential obtained are well distinguishable based on their post-stimulus latencies and durations.

The sodium channel blockers in general and among them tolperisone and eperisone, which are closely related both in structure and activity, show considerable spinal reflex inhibitory effect in the hemisected spinal cord preparation, in vitro. This preparation is ideal for the investigation of pharmacodynamic interactions between two substances, since metabolic factors take no part in them.

Figure 2:
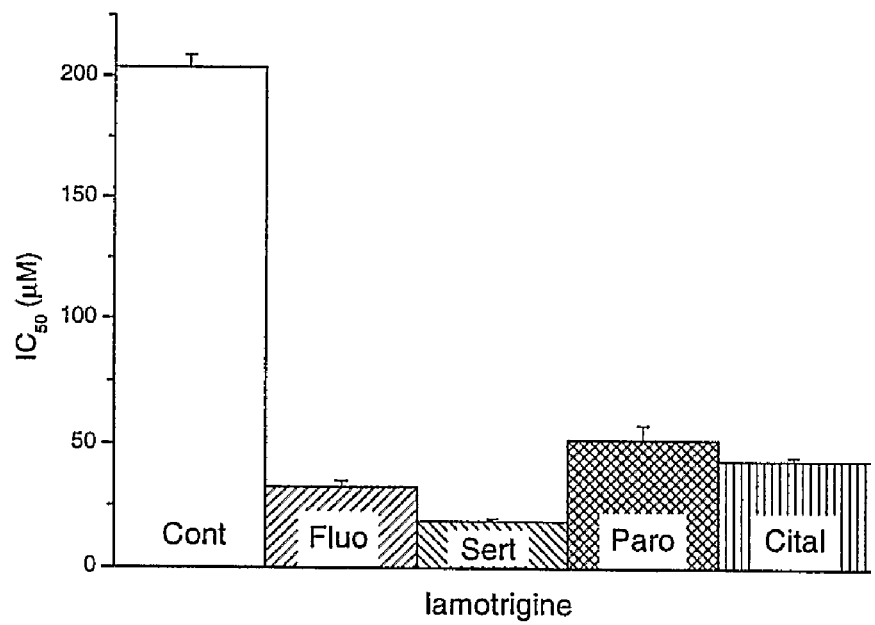
Figure 3:
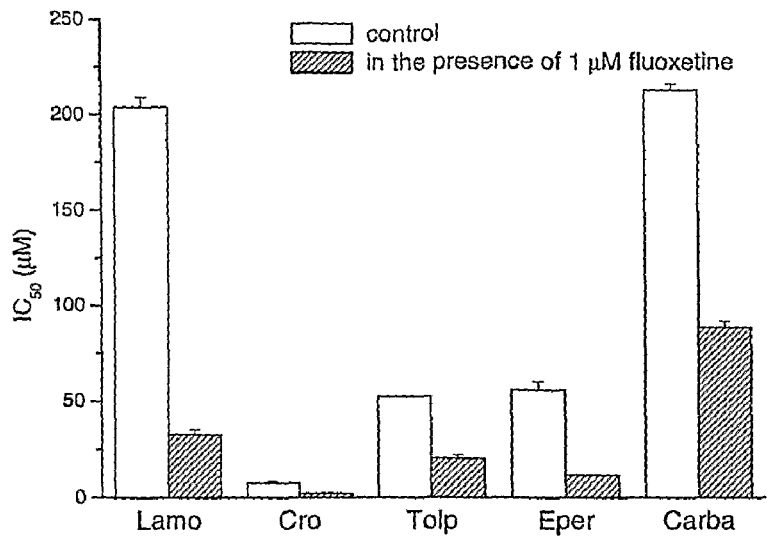

The results are shown in FIGS. 1, 2 and 3. Namely, in FIG. 1. potentiating effect of different serotonin uptake inhibitors on the reflex inhibitory activity of crobenetine, a sodium channels blocker is shown. Cont (control)=effect of crobenitine in itself; as well as in the presence of fluoxetine (Fluo; 1 μM), sertraline (Sert; 0.5 μM), paroxetine (Paro; 10 nM) and citalopram (Cital; 5 nM).

In FIG. 2. potentiating effect of different serotonin uptake inhibitors on the reflex inhibitory activity of lamotrigine, a sodium channel blocker is shown. Cont (control)=effect of lamotrigine in itself; as well as in the presence of fluoxetine (Fluo; 1 μM), sertraline (Sert; 0.5 μM), paroxetine (Paro; 10 nM) and citalopram (Cital; 5 nM).

In FIG. 3. potentiating effect of a serotonin uptake inhibitor (1 μM fluoxetine) on the reflex inhibitory activity of different sodium channel blockers is shown, wherein the reflex inhibitory effects of lamotrigine (Lamo), crobenetine (Cro), tolperisone (Tolp), eperisone (Eper) and carbamazepine (Carba) without and with 1 μM fluoxetine can be seen.

Addition of the serotonin uptake inhibitor induced significant increase in the sodium channel blocking activity in each case.

Alterations in the potencies of the sodium channel blockers at elevated serotonin tone were also measured in vivo, namely their tremor inhibitory action was tested in the GYKI 20039-induced tremor test.

Tremor Test

Inhibitory effect on drug-induced tremor in mice is a good indication of muscle relaxant efficacy of compounds in humans. Tremor can be induced by administration of GYKI 20039 (3-(2,6-diclorophenyl)-2-iminothiazolidine). The method was published by Kocsis P., Tarnawa I., Kovacs Gy., Szombathelyi Zs., Farkas S., 2002; Acta Pharmaceut. Hung., 72:49-61; U.S. Pat. No. 5,340,823, 1994, U.S. Pat. No. 5,198, 446, JP 1992270293, EP 0468825, 1990 HU 4647.

Our experiments revealed that GYKI 20039 induces intensive tremor at 10 mg/kg intraperitoneal dose in mice, which lasts for 30-60 minutes and reaches its maximum between the 4th-8th minutes. Its mode of action is not entirely clear, but its structural similarity to LON-954, a tremorogen compound, suggests the involvement of the descending dopaminergic and serotoninergic systems (Mohanakumar, K. P., Ganguly, D. K., 1989; Brain Res. Bull. 22: 191-5).

GYKI 20039 induced tremor can be dose-dependently inhibited by muscle relaxant drugs with different modes of action, therefore it is a suitable method for comparing the muscle relaxant efficacy of drugs. The model has been validated using several different muscle relaxant drugs used in the clinical practice. All of them produced dose-dependent inhibitory effect, which correlated with the clinical antispastic efficacy of the muscle relaxant drugs.

In our study sodium channel blockers proved to possess tremor inhibitory action and the change in their potency in the presence of elevated serotonin level was also determined. Tests were carried out in male NMRI mice (19-21 g), the active substances were administered i.p., simultaneously.

Figure 4:
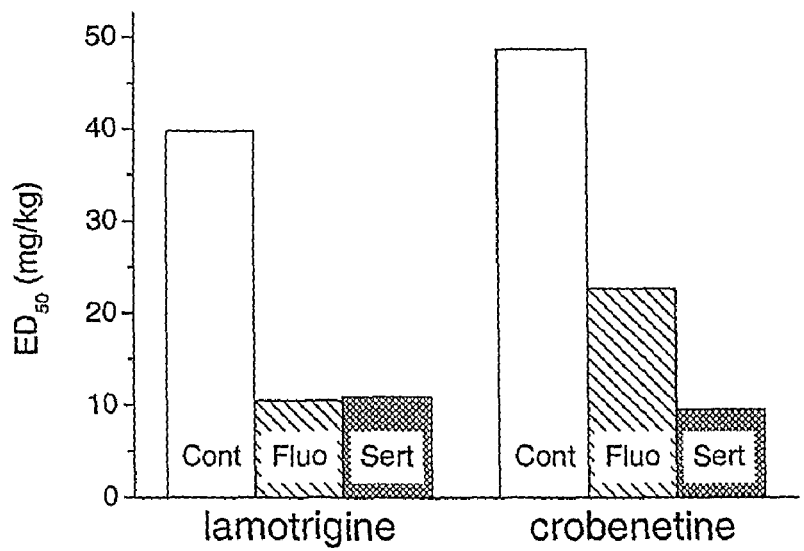

In FIG. 4. effects of sodium channel blockers lamotrigine and crobenetine as well as the increase of their effectiveness when a serotonin uptake inhibitor is present in a dosage producing no significant effect in itself are shown. Namely, the $ID_{50}$ values obtained in the tremor test are plotted for lamotrigine and crobenetine alone (Cont) and together with 10 mg/kg fluoxetine (Fluo) or 10 mg/kg sertraline (Sert); all substances were administered i.p.

Experiments with combinations containing the active agents in a fixed ratio were also performed. Increased potency was found in this case, too. In Table 1 below increase in potency of a sodium channel blocker (lamotrigine) achieved by addition of fix ratios of a serotonin uptake inhibitor (fluoxetine) is shown.

TABLE 1

| components | ratio | $ID_{50}$ (i.p.) (calculated for the sodium channel blocker in the combination) |
|---|---|---|
| Lamotrigine | — | 39.79 mg/kg |
| Lamotrigine:fluoxetine | 10:1 | 22.9 mg/kg |
| Lamotrigine:fluoxetine | 10:2 | 15.3 mg/kg |

Inhibition of Maximal Electroshock Seizures

Inhibition of maximal electroshock seizures (MES; Swinyard, E. A., Brown, W. C., Goodman L. S. Comparative assay of antiepileptic drugs in mice and rats. Journal of Pharmacology and Experimental Therapeutics 106, 319-330; 1952) shows the antiepileptic potency of a compound. Experiments in this respect were carried out on male NMRI mice (19-21 g). Pretreatment of the animals with SSRI compounds caused a substantial increase in the potency of the sodium channel blockers, while the SSRI compounds administered alone at this dosage were practically ineffective in this test.

Table 2 below shows the increased potency of sodium channel blockers in the presence of serotonin reuptake inhibitors having no significant effect by themselves. Serotonin uptake inhibitors were administered i.p. 45 minutes, while sodium channel blockers 30 minutes prior to the electroshock.

TABLE 2

| | $ID_{50}$ (MES inhibition in mice) | | |
|---|---|---|---|
| | | with | |
| | alone | fluoxetine (10 mg/kg) | sertraline (10 mg/kg) |
| lamotrigine | 4.5 | 1.3 | 1.4 |
| crobenetine | >>20 | 17.0 | 15.5 |

Our results show that serotonin uptake inhibitors potentiate the effect of antiepileptics with sodium channel blocking mechanism of action. On the other hand, in the rotarod test by which the motor side effect was studied this potentiating effect was far less expressed showing that the side effect profile has also been improved. Thus, the combined use of the two substances resulted in a more potent pharmaceutical having a more favourable side effect profile.

Rotarod Test

By the rotarod test (Dunnham, N. W., Miya, T. S. J. Am. Pharm. Assoc. 46, 208, 1957) impaired coordination and disorders of the voluntary movement as possible side effects can be studied. In this respect the change in the potency of the voltage-dependent sodium channel blockers caused by the serotonin uptake inhibitors was far less pronounced, resulting in a more favourable side effect profile of the combinations compared to that of the parent compounds.

The tests were carried out using male NMRI mice (19-21 g). Experiments performed with different pretreatment times produced similar results. Table 3 below indicates a slightly increased potency of sodium channel blockers in the presence of serotonin reuptake inhibitors.

TABLE 3

| | $ED_{50}$ (mg/kg), rotarod test in mice | | | | | |
|---|---|---|---|---|---|---|
| | alone | | In combination with | | | |
| | | | fluoxetine (10 mg/kg) | | sertraline (10 mg/kg) | |
| | −20 min | −35 min | −20 min | −35 min | −20 min | −35 min |
| lamotrigine | 34.3 | N.T.* | 28.5 | 31.1 | 31.9 | 30.8 |
| crobenetine | 68.1 | N.T.* | 38.6 | 51.0 | 36.8 | 53.1 |
| fluoxetine | 43.5 | 45.8 | | | | |
| sertraline | 111.5 | 120.4 | | | | |

*not tested

Phenylquinone-induced Acute Pain (Writhing Test)

The method used was described by Hendershot and Forsaith in 1959. (Kazuko Goto et al. Analgesic Effect of Mofezolac, a Non-Steroidal Anti-Inflammatory Drug, Against Phenylquinone-Induced Acute Pain in Mice. Prostaglandins & other Lipid Mediators 56: 245-254; 1998, Prem Prakash Singh et al. Acetic Acid and Phenylquinone WrithingTest: A Critical Study in Mice. Meth and Find Exptl Clin Pharmacol 5(9): 601-606; 1983.) Acute pain was induced by injecting phenylquinone, an irritant, into the abdominal cavity (0.02% solution, 0.1 ml/10 g bodyweight). Fluoxetine was administered 15 minutes prior to lamotrigine (i.p). Experiments were performed in male NMRI mice (19-21 g).

Figure 5:
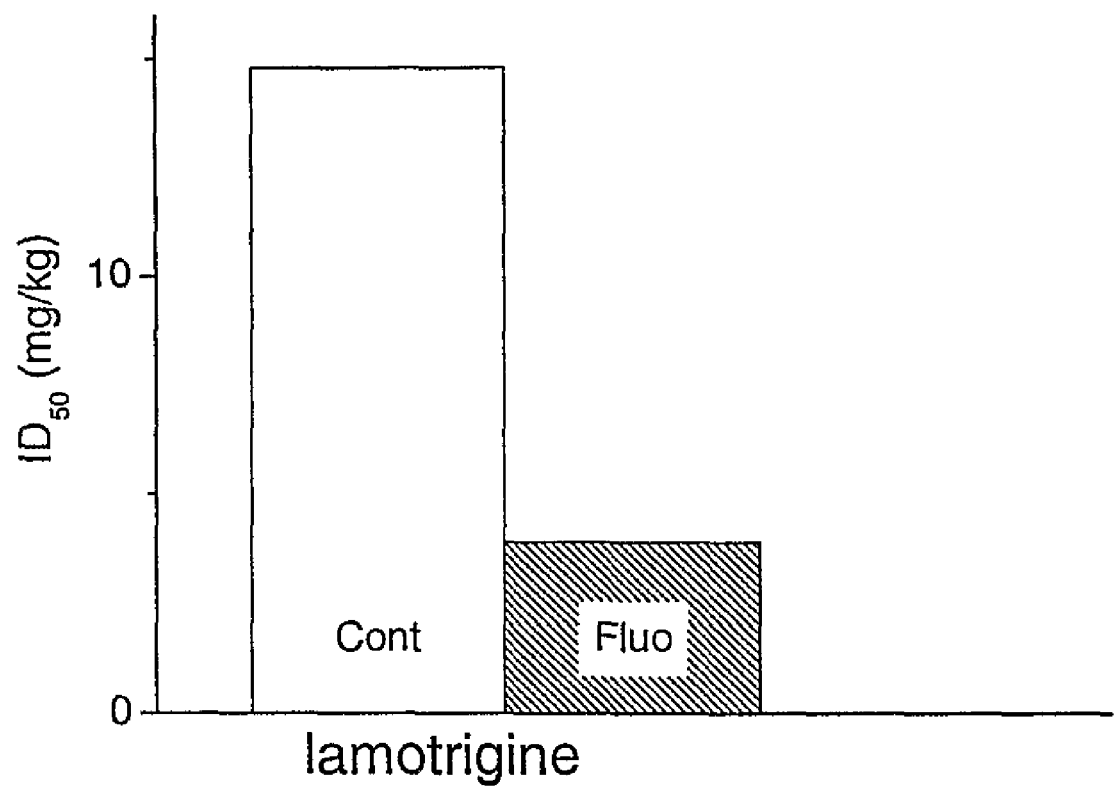

Increase in the analgesic potency of lamotrigine, a sodium channel blocker, in the presence of a serotonin uptake inhibitor is shown in FIG. 5, wherein $ID_{50}$ values obtained in the whrithing test are plotted for lamotrigine alone (Cont) and in combination with 10 mg/kg fluoxetine (Fluo).

The invention claimed is:

1. A pharmaceutical composition comprising a sodium channel blocker selected from the group consisting of lamotrigine and crobenetine, in combination with a selective serotonin uptake inhibitor selected from the group consisting of fluoxetine, paroxetine, sertraline, escitalopram and citalopram, wherein said composition has a potentiating effect.

2. A pharmaceutical composition according to claim 1, wherein the selective serotonin uptake inhibitor is fluoxetine and the sodium channel blocker is lamotrigine.

3. A pharmaceutical composition according to claim 1, wherein the selective serotonin uptake inhibitor is fluoxetine and the sodium channel blocker is crobenetine.

4. A pharmaceutical composition according to claim 1, wherein the selective serotonin uptake inhibitor is sertraline and the sodium channel blocker is lamotrigine.

5. A pharmaceutical composition according to claim 1, wherein the selective serotonin uptake inhibitor is sertraline and the sodium channel blocker is crobenetine.

6. A method for the treatment of chronic pain or epilepsy in a mammal comprising administering to a mammal in need of the treatment a therapeutically effective amount of pharmaceutical composition comprising a sodium channel blocker selected from the group consisting of lamotrigine and crobenetine, and a selective serotonin uptake inhibitor selected from the group consisting of fluoxetine, paroxetine, sertraline, escitalopram and citalopram, wherein said treatment has a potentiating effect.

7. A method according to claim 6, wherein the selective serotonin uptake inhibitor is fluoxetine and the sodium channel blocker is lamotrigine.

8. A method according to claim 6, wherein the selective serotonin uptake inhibitor is fluoxetine and the sodium channel blocker is crobenetine.

9. A method according to claim 6, wherein the selective serotonin uptake inhibitor is sertraline and the sodium channel blocker is lamotrigine.

10. A method according to claim 6, wherein the selective serotonin uptake inhibitor is sertraline and the sodium channel blocker is crobenetine.

* * * * *